(12) United States Patent
Deimling

(10) Patent No.: US 7,340,290 B2
(45) Date of Patent: Mar. 4, 2008

(54) MAGNETIC RESONANCE TOMOGRAPHY APPARATUS AND METHOD FOR OPERATING SAME FOR IMAGE GENERATION

(75) Inventor: Michael Deimling, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1023 days.

(21) Appl. No.: 10/135,475

(22) Filed: Apr. 30, 2002

(65) Prior Publication Data

US 2002/0183612 A1 Dec. 5, 2002

(30) Foreign Application Priority Data

May 4, 2001 (DE) ................ 101 21 802

(51) Int. Cl.
*B61B 5/05* (2006.01)
(52) U.S. Cl. ............ 600/410; 382/128; 382/130; 382/131; 382/132; 382/240; 382/254
(58) Field of Classification Search ........... 600/410; 382/128, 169, 173, 130–32, 240, 254–75
See application file for complete search history.

(56) References Cited

U.S. PATENT DOCUMENTS

| | | | | |
|---|---|---|---|---|
| 4,463,375 A | * | 7/1984 | Macovski | 378/98.12 |
| 4,661,986 A | * | 4/1987 | Adelson | 382/154 |
| 4,789,933 A | * | 12/1988 | Chen et al. | 382/128 |
| 5,034,692 A | * | 7/1991 | Laub et al. | 324/309 |
| 5,297,551 A | * | 3/1994 | Margosian et al. | 600/410 |
| 5,337,000 A | * | 8/1994 | Bruder | 324/309 |
| 5,490,516 A | * | 2/1996 | Hutson | 600/508 |
| 5,627,469 A | * | 5/1997 | Hong et al. | 324/309 |
| 5,814,991 A | | 9/1998 | Deimling | |
| 6,392,412 B1 | * | 5/2002 | Nauerth | 324/320 |
| 6,470,202 B2 | * | 10/2002 | Rosenfeld | 600/410 |

OTHER PUBLICATIONS

"Bildgebende Sequenzen in der Kernspintomographie und ihre klinische Anwendung," Nitz, electromedica 65, No. 1 (1997).

* cited by examiner

*Primary Examiner*—Brian L. Casler
*Assistant Examiner*—Parikha S. Mehta
(74) *Attorney, Agent, or Firm*—Schiff Hardin LLP

(57) ABSTRACT

In a method and apparatus for generating an image from magnetic resonance signals, two image matrices generated from magnetic resonance signals are added to or subtracted from one another pixel-by-pixel, to generate a further image therefrom. The magnitude added or subtracted for each picture element is formed by multiplication of a magnitude value of the second image matrix by a weighting factor. The weighting factor is dependent on the magnitude value of the second image matrix such that it is higher given a high magnitude value than for a low magnitude value. The magnitude noise is decreased compared to a linear addition or subtraction, and uncontrolled signal reductions are avoided. An exponent in the power of the magnitude value of the second image matrix a signal-dependent weighting factor can be set at an input device.

67 Claims, 3 Drawing Sheets

MAGNETIC RESONANCE TOMOGRAPHY APPARATUS AND METHOD FOR OPERATING SAME FOR IMAGE GENERATION

BACKGROUND OF THE INVENTION

1. Field of the Invention

The present invention is directed to a method for generating an image from magnetic resonance signals of the type wherein a first image matrix is generated from first magnetic resonance signals and a second image matrix is generated from second magnetic resonance signals, an overall magnitude is formed for each picture element by adding or subtracting a magnitude dependent on the appertaining magnitude value of the second image matrix to or from a magnitude that is dependent on the magnitude value of the corresponding picture element of the first image matrix, with the overall magnitudes being employed for generating the image.

The present invention also is directed to a method for generating an image from magnetic resonance signals of the type wherein a first group of location coded magnetic resonance signals and a second group of location coded magnetic resonance signals different therefrom are received, overall signals are formed from the respective magnetic resonance signals with coinciding location coding of the first group and the second group, wherein the overall signal is formed by adding or subtracting a second magnitude dependent on the appertaining magnetic resonance signals of the second group to or from a first magnitude that is dependent on the magnetic resonance signals of the first group, and wherein the overall signals are utilized for reconstruction of the image.

The invention also is directed to a magnetic resonance tomography apparatus for the implementation of the method and to a data processing system for a magnetic resonance tomography apparatus.

2. Description of the Prior Art

It is known in the field of magnetic resonance tomography to add or subtract two congruent images generated in different ways, i.e. images that constitute the same portion in the examination subject. The magnitude value of the appertaining picture element of the second image is added to or subtracted from a magnitude value of a picture element of the first image for each picture element. In this way, contrasts can be intensified, new contrasts can be generated or image artifacts can be avoided. The congruent images are generated from a common pulse sequence, i.e. they derive from a readout sequence with common phase coding.

The picture elements are represented in the images as complex numbers, and the magnitude value of a complex number $a+bi$ is $(a^2+b^2)^{1/2}$ (also called the absolute value).

An image addition is implemented, for example, in the DESS technique (Double Echo Steady State). A specific pulse sequence is generated with which a FISP echo as well as a PSIF echo can be read out within a readout train. The DESS method is disclosed, for example, in the article by W. Nitz in electromedica 65 (1997), No. 1. The FISP echo (Fast Imaging with Steady State Precession) is a gradient echo. In the preferred field of application of orthopedics, it supplies a T1/T2 contrast typical of steady state techniques (SSFP pulse sequences). The PSIF echo arises from a FSIP pulse sequence that sequences backwards. This is also referred to as a quasi-spin echo. Dependent on the repetition time, it carries a strong T2 contrast. The magnitude addition of the image resulting from the FISP echo with the image resulting from the PSIF echo supplies an image with good anatomy and very good emphasis of fluid, for example the synovil fluid, at pathological locations.

An image subtraction is known, for example, from German OS 196 16 387. The HIRE method (high-intensity reduction sequence) is disclosed therein. After an excitation, two groups of magnetic resonance signals are acquired in two time spans at a different intervals from the excitation. An image is acquired on the basis of the signal differences of respective magnetic resonance signals of the first and second groups with coinciding location coding. The first group of magnetic resonance signals or echos, which is acquired shortly after the excitation, results in an image with normal T2 weighting. The second group of magnetic resonance signals or echos, which is acquired later in a time span than the first group and wherein a tissue part having a longer T2 time constant supplies the significant signal contribution, yields a highly T2-weighted image. A fluid such as, for example, the cerebral spinal fluid (CSF), leads to a very high signal contribution in a normally T2-weighted image, for example to a significantly higher signal contribution in the brain than the other brain areas. In the normally T2-weighted image acquired shortly after the excitation, a neighboring image region would be over-shadowed by this high signal contribution of the CSF and the resolution would thus be locally diminished. Moreover, artifacts referred to as CSF flux or pulsation artifacts also arise. When the highly T2-weighted image acquired at a later point in time is subtracted from the magnitude image acquired shortly after excitation, then an image results that is still T2-weighted and wherein the fluid, particularly CSF, is highly suppressed.

One disadvantage of the known image subtraction or image addition methods is that the aggregate noise increases approximately by a factor of $\sqrt{2}$.

SUMMARY OF THE INVENTION

An object of the present invention is to provide a method and a nuclear magnetic resonance tomography apparatus wherein this disadvantage is avoided.

In a method of the type initially described, this object is inventively achieved in that the magnitude for each picture element of the second image matrix is formed by multiplication of the magnitude value of the second image matrix by a weighting factor, the weighting factor being dependent on the magnitude value of the second image matrix such that it is higher for a high magnitude value than for a low magnitude value.

The second magnitude thus is formed for each picture element such that its contribution to the respective overall magnitude is lower given a low value of the magnitude value of the second image matrix than it would be given a linear addition or subtraction of the magnitude values of the two image matrices, and such that it is essentially as large as it would be given a linear addition or subtraction when the magnitude value of the second image matrix is high. In the described method, a self weighting of the magnitude value of the second image matrix employed for the correction or improvement of the image quality of the first image matrix is made. In other words: the second magnitude weights itself dependent on the local image conditions. This results in only those picture elements that have a high signal magnitude being superimposed with large contribution on the respective picture element of the first image matrix. Picture elements having a slight signal contribution lead to no significant influence on the magnitude value of the first image matrix. In other words, only the picture elements that are in fact useable for the correction or improvement of the first image matrix are filtered out of the second image matrix pixel-by-pixel. The remaining pixels remain essentially out of conserderation, or at least are weighted less. This results in the advantage that the noise is lower in the resulting image then it would be given a linear addition or subtraction of the two images.

Another advantage is that an uncontrolled signal reduction or reduction of the image quality is avoided in regions where there is actually nothing to correct or improve.

Preferably, the first image matrix is reconstructed from a first group of location-coded nuclear magnetic resonance signals by means of Fourier transformation, and the second image matrix is likewise reconstructed by Fourier transformation from a second group of location-coded nuclear magnetic signals different from the first group. In particular, a magnitude formation occurs after the Fourier transformation. The method of the invention can be implemented not only with Fourier-transformed values or magnitude values but also can be implemented using raw data acquired directly from the magnetic resonance signals. This is explained in greater detail below in conjunction with the method according to the second embodiment.

The weighting factor can be realized, for example, by a mathematical step function that sets the weighting factor to a low value or to zero below a defined threshold of the magnitude value of the second image matrix.

In a preferred version of the first embodiment of the method, the second magnitude is formed for every picture element such that it is dependent on the magnitude value of the second image matrix in non-linear fashion, particularly steadily non-linear, with the same non-linear mathematical function being employed for the formation of the overall magnitudes of all picture elements.

Preferably, the second magnitude for every picture element is formed such that it is dependent on a power of the magnitude value of the second image matrix, with the exponent being the same for all picture elements and is greater then 1 (one), particularly greater than or equal to 2. A steady non-linear dependency of the weighting factor on the magnitude value of the second image matrix is used for this purpose. Compared to a step function, this version has the advantage that image artifacts are avoided.

In a preferred embodiment, the exponent in the power of the magnitude value of the second image matrix is varied, particularly in order to achieve an optimally high contrast in the image and/or an optimum correction of the first image matrix with the second image matrix. The variation of the exponent is undertaken, for example, by a computer program or manually by an operator.

Preferably, the exponent in the power of the magnitude value of the second image matrix is greater in the second magnitude than an exponent of a power of the magnitude value of the first image matrix. The self-weighting is further intensified as a result.

The method is not limited to the superimposition of two image matrices. One or more further image matrices can be employed for generating the image in the same way as the first image matrix or as the second image matrix. This has the advantage that the advantageous regions of a number of image matrices are imported into the first image matrix by the described self-weighting. The two image matrices and the further image matrices that are possibly employed, are congruent at least in a sub-region and preferably result from a pulse sequence deriving from a common radio-frequency excitation pulse.

In another preferred embodiment of the method, the first image matrix is more signal-intensive, particularly more signal-intensive on average, than the second image matrix. In particular, the first image matrix is the most signal-intensive image matrix that can be generated from a pulse sequence, i.e. from a common readout train.

The method of the invention is preferably applied to the initially described HIRE method or to the initially described DESS method, so that these two known, linearly functioning superimposition methods are provided with a self-weighting.

For realizing a self-weighting HIRE method, the overall magnitudes are formed by subtraction of the second magnitude from the first magnitude, with those magnetic resonance signals that would be subtracted from one another given application of a high-intensity reduction pulse sequence being employed for generating the two image matrices.

As initially set forth, the HIRE method is especially suited for the examination of a subject that contains a first tissue having a first T2 time constant as well as a second tissue having a significantly longer, second T2 time constant. For such a tissue, the magnetic resonance signals in the method of the invention preferably are acquired for both image matrices during the time span wherein the cross-magnetization that has arisen after an excitation decreases with the respective T2 time constant, and the magnetic resonance signal for the first image matrix is acquired soon after the excitation, and the magnetic resonance signal for the second image matrix is acquired in a time interval wherein the second tissue supplies the significant signal contribution.

With application of the method of the invention to the HIRE pulse sequence, the advantage is achieved that a determinant image subtraction only occurs in those regions of the first image matrix wherein the magnitude of the second image matrix is large. In the examination of the brain, for example, this applies to the aforementioned cerebral spinal fluid (CSF). By contrast, only a slight magnitude is subtracted in the region of an edema (seat of a disease with surrounding accumulation of fluid) or in the region of normal tissue (for example, muscle tissue as well), so that the signal-to-noise ration (S/N) of these regions is not unnecessarily deteriorated. With a summary image subtraction, regions would also have their signal value reduced dependent on their local T2 values, so that, for example, an edema would disadvantageously have a SN similar to the normal, surrounding tissue.

In another preferred embodiment, the method of the invention is applied to the known DESS method. To this end, the overall magnitudes are formed by addition of the first magnitude and of the second magnitude, with those magnetic resonance signals being employed for generating the two image matrices that would in a double echo steady-state pulse sequence (DESS method).

Specifically, the magnetic resonance signal for the first image matrix is generated from a gradient echo, particularly from a fast imaging with steady state precession echo (FISP echo), and the magnetic resonance signal for the second image matrix is generated from a quasi-spin echo, particularly from a PSIF echo, as would arise given an inverse FISP pulse sequence (PSIF pulse sequence), so that the two magnetic resonance signals derive from the same DESS pulse sequence.

In the weighted image addition compared to linear, summary image addition, only those image regions are added wherein the second image has a strong signal and, in particular, a higher contrast than the first image. By contrast thereto, only a very slight portion of the second image is added to the first image in image regions having low signal-to-noise ratio (SN), for example in muscle tissue. The resulting image quality is therefore improved compared to a linear image addition.

In a summary image addition, regions, for example muscle tissue, having a very low SN would also be added, so that the resulting image quality would be diminished.

In the method of the invention, the overall magnitude of a picture element is particularly formed using an expression having the form $$X_i^f \pm P \cdot Y_i^e$$

wherein $X_i$ is the magnitude value of a picture element of the first image matrix, $Y_i$ is the corresponding magnitude value of the second image matrix, and f and e are the exponents of the power of the appertaining magnitude values and P is a proportionality factor, and wherein e is greater than 1 (e>1) and, preferably, e is greater than f (e>f). Such a calculating rule can be programmed in a computer in a simple way without significant image artifacts being generated.

In another preferred development, a scaling factor is employed for forming the second magnitude such that the value of the second magnitude is not greater for any picture element than the magnitude value of the second image matrix. The scaling factor thus normalizes the second magnitude such that the maximum case would add or subtract no more than would be the case given a linear addition or subtraction. In the maximum case, i.e. given a high magnitude value in the second image matrix, the method of the invention accordingly leads to a mathematical operation that is comparable to the described, linear procedure. By contrast, the magnitude of the second image matrix in the resulting overall image is suppressed in comparison to the linear operation in the case of low magnitude values of the second image matrix.

Preferably, the scaling factor is formed from a maximum value of the magnitude values of the picture elements of the first image matrix.

In a preferred embodiment the scaling factor is determined from a maximum value of the magnitude values of the picture elements of a number of image matrices, whereby the image matrices being generated from pulse sequences of the same type and, in particular, derived from a common three-dimensional image. As a result, it is easier to view a series of 2D images.

For calculating the second magnitude, a weighting factor that is identical for all picture elements can be additionally employed that does not exhibit the value 1, particularly a value greater than 1.

This weighting factor is varied in a preferred version of the method, in order to achieve an optimally high contrast in the image and/or an optimum correction of the first image matrix by the second image matrix. The variation ensues either manually or automatically by computer.

The object directed to a magnetic resonance tomography apparatus is inventively achieved in a nuclear magnetic resonance tomography apparatus in which a computer program for the implementation of the method is loaded.

The magnetic resonance tomography apparatus preferably is equipped with an input device with which the exponent in the power of the magnitude value of the second image matrix and/or the weighting factor can be set.

As already mentioned, the weighted addition or subtraction as implemented in the first embodiment of the method of the invention can be accomplished not only at the magnitude values of image matrices but can also be accomplished at the magnetic resonance signals per se, i.e. at the raw data.

With the initially cited, second embodiment of the invention, the method-related object is achieved by the second magnitude being formed by multiplication of the corresponding magnetic resonance signal of the second group with a weighting factor, the weighting factor being dependent on the magnetic resonance signal of the second group such that it is higher for a high magnetic resonance signal than for a low magnetic resonance signal.

The second magnitude thus is formed such that its contribution to the overall signal is lower given a small value of the magnetic resonance signal of the second group than it would be given a linear addition or subtraction of the magnetic resonance signals of the two groups, and such that it would be essentially of the same size as in the linear addition or subtraction given a high value of the magnetic resonance signal of the second group.

Preferably, the second magnitude is formed such that it is dependent on the magnetic resonance signal of the second group in non-linear fashion, particularly steadily non-linear, with the same non-linear function being employed for the formation of all overall signals.

In particular, the second magnitude is formed such that it is dependent on a power of the magnetic resonance signal of the second group, the exponent being of the same size for all overall signals and is greater than 1, particularly greater than or equal to 2.

Particularly good results are achieved when the exponent in the power of the magnetic resonance signal of the second group is higher in the second magnitude than in exponent in a power of the magnetic resonance signal of the first group in the first magnitude.

A raw data matrix can be formed from the overall signals determined in this way, a matrix yielding the image being generated therefrom from Fourier transformation.

DESCRIPTION OF THE PREFERRED EMBODIMENTS

Figure 1:
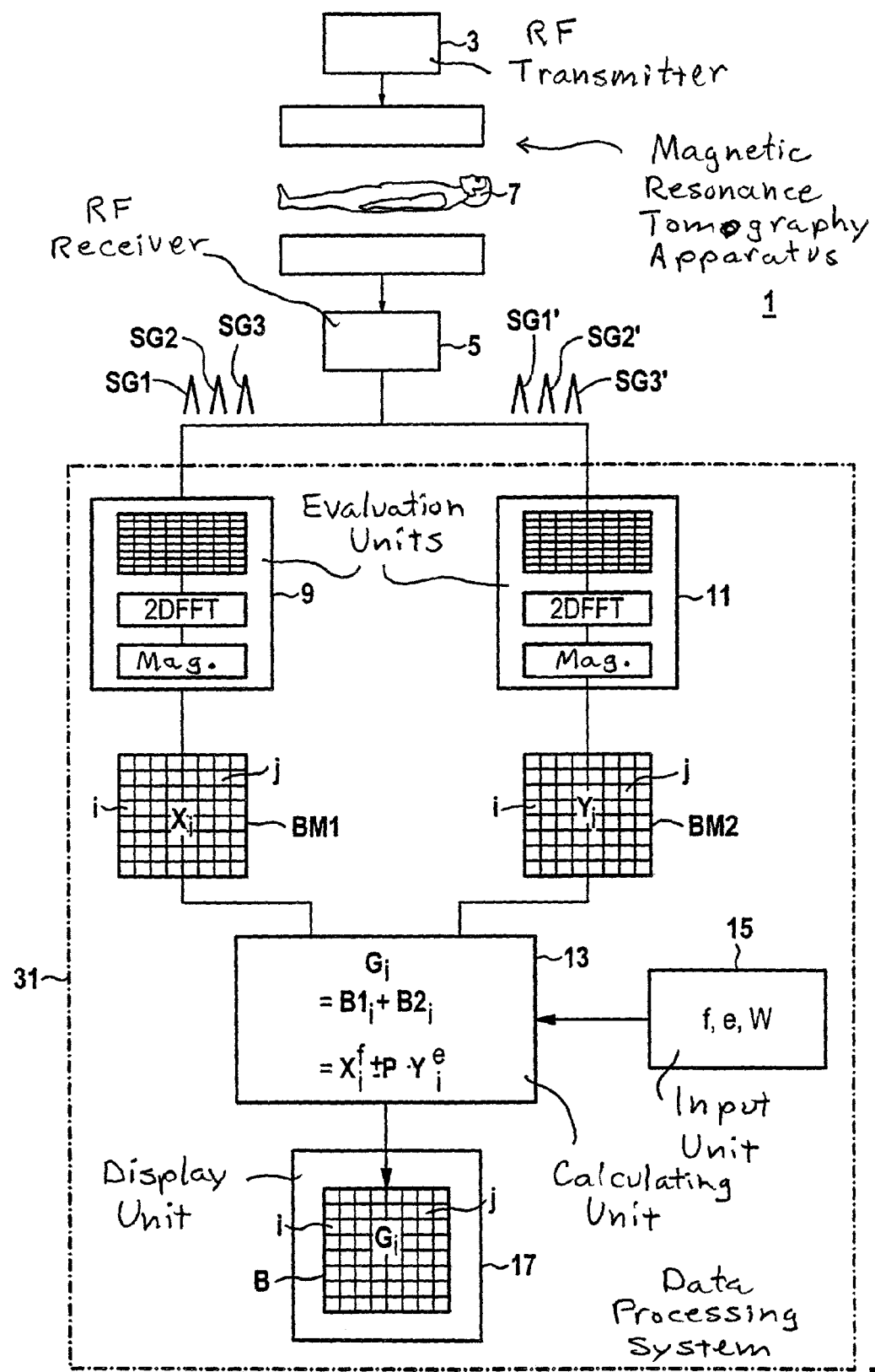
FIG. 1 is a flowchart of an exemplary first embodiment of the inventive method.

FIG. 1 schematically shows the executive sequence of the method and the required components as well. In a magnetic resonance tomography apparatus 1 having a conventional magnet and gradient system (not explicitly shown), radio-frequency pulses are emitted into an examination subject 7 with a radio-frequency transmitter 3 and the magnetic resonance signals SG1, SG2, SG3 . . . and SG1', SG2', SG3' . . . are received with a radio-frequency receiver 5. The magnetic resonance signals SG1 through SG3 are sampled in an evaluation unit 9, digitized, and the digital values are entered row-by-row into a raw data matrix. The magnetic resonance signals SG1' through SG3' are processed in the same way in an evaluation unit 11 and are entered into a second raw data matrix. Both raw data matrices are subjected to a two-dimensional Fourier transformation (2D FFT), and magnitude values $X_i$ and $Y_i$ are calculated from the complex values acquired in this way. Two image matrices BM1 and BM2 having a number of picture elements i are thus obtained, whereby $X_i$ references the magnitude value of a picture element i of the first image matrix BM1 and $Y_i$ references the magnitude value of a picture element i of the second image matrix BM2.

The two image matrices BM1 and BM2 are supplied to a calculating unit 13 that is in communication with an input unit 15. In the calculating unit 13, the final image or image B that can be viewed by the user and that is displayed in a display unit 17 is calculated. The individual picture elements i of the image B are respectively calculated as follows as overall magnitude $G_i$ from a first magnitude $B1_i$ and from a second magnitude $B2_i$:

$$G_i = B1_i \pm B2_i \quad (Eq. 1)$$

i.e., either the second magnitude $B2_i$ is subtracted from the first magnitude $B1_i$ or the two magnitudes $B1_i$, $B2_i$ are added.

The first magnitude $B1_1$ is dependent on the magnitude value $X_i$ of the corresponding picture elements i of the first image matrix $BM_1$ and, in particular, is identical thereto. According to the invention, the second magnitude $B2_i$ for each picture element i is formed by multiplication of the corresponding magnitude value $Y_i$ of the second image matrix BM2 by a weighting factor F, the weighting factor F being dependent on the magnitude value $Y_i$ of the second image matrix BM2:

$$G_i = X_i \pm F(Y_i) \cdot Y_i \quad (Eq. 2)$$

The weighting factor F can, for example, be formed by a mathematical step function that has a lower constant value as result below a specific threshold than above the threshold. In the preferred embodiment shown here, the weighting factor F is dependent via a power's law on the magnitude value $Y_i$, of the second image matrix BM2, so that, for example, the following dependency exists:

$$G_1 = X_i^f \pm P \cdot Y_i^e \quad (Eq. 3)$$

wherein P is a location-independent or pixel-independent proportionality factor that is not dependent on any of the magnitude values $X_i$, $Y_i$, and e and f are the exponents of the powers of the appertaining magnitude values $X_i$, $Y_i$.

For explaining the function of the calculating rule for the overall magnitudes $G_i$, Equation 3 is subsequently brought into a different form for the case f=1:

$$G_i = X_i \pm W \cdot \left(\frac{Y_i}{X_{max}}\right)^\lambda \cdot Y_i \quad (Eq. 4)$$

wherein, W is a location-independent or pixel-independent weighting factor and the term with the exponent references a scaling factor S according to:

$$S = \left(\frac{Y_i}{X_{max}}\right)^\lambda \quad (Eq. 5)$$

In particular, the weighting factor lies in the range from 0.5 through 10.

The exponent $\lambda$ in the scaling factor S is related via the relationship $$\lambda = e - 1 \quad (Eq. 6)$$

with the exponents e from Equation 3. The exponent $\lambda$ can assume an arbitrary value that is greater than 0 and is preferably greater than 1.

The quantity $X_{max}$ is a maximum value of the magnitude values $X_i$ of the picture elements i of the first image matrix BM1. In that case wherein, given the assistance of the gradient coil, a plurality of slices or partitions were successively excited in the direction of their gradients, in that case wherein data for a three-dimensional image are thus present, the maximum value $X_{max}$ is formed as maximum of the magnitude values of all picture elements of the three-dimensional image. In other words: $X_{max}$ is the global maximum image intensity of all n*m*N pixels (n*m: in-plane matrix resolution; N: number of slices or partitions, for example n=m=256, N=64).

The first image matrix BM1 was selected such that it is more signal-intense than the second image matrix BM2. The following therefore applies for all picture elements i: $Y_i \leq X_i$. It follows therefrom that the scaling factor S for all picture elements i is smaller than 1. The scaling factor S is such that the weighted, second magnitude $B2_i$ is lower, the lower a magnitude value $Y_i$ of the second image matrix BM2 becomes lower.

For forming the overall magnitudes $G_i$, other mathematical operations can be additionally utilized in additional to a subtraction or/and an addition, insofar as a self-weighting of the magnitude value $Y_i$ of the second image matrix BM2 is merely present. For example, the following mathematical operations have proven especially suitable:

$$G_1 = \left[X_i^{r+1} \pm X_i^r \cdot W \cdot \left(\frac{Y_i}{X_{max}}\right)^\lambda \cdot Y_i\right]^{1/1} \quad (Eq. 7)$$

when r is an arbitrary real number

For the case r=1 and for the case of addition of the two magnitudes $B1_i$, $B2_i$, the following weighting is obtained:

$$G_i = \sqrt{X_1^2 + X_i \cdot W \cdot \left(\frac{Y_i}{X_{max}}\right)^\lambda \cdot Y_i} \quad (Eq. 8)$$

This calculating rule is especially suited for self-weighting in a DESS method. In this case, the FISP signal is respectively utilized for the magnitude value $X_i$ of the first image matrix BM1 and the PSIF signal is utilized for the magnitude value $Y_i$ of the second image matrix BM2. In a region I (see FIG. 2) of the examination subject 7 having relatively high PSIF signal, for example in the region of fluid, water or CSF, the signal magnitude of the PSIF signal is added to the FISP signal with the scaling factor S that is then approximately equal to 1. In a region II, for example in musculature, the scaling factor S magnitudes to only approximately $(1/10)^2 = 0.01$, i.e. the signal contribution of the PSIF signal remains below the magnitude noise limit.

Figure 2:
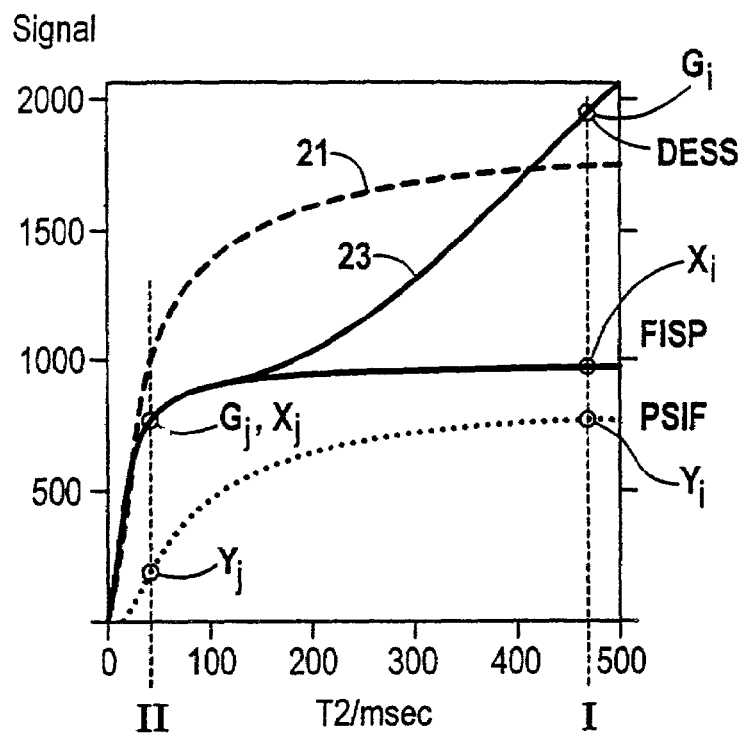
FIG. 2 illustrates a simulation of the method according to FIG. 1 employed in a DESS method.

FIG. 2 shows the result of the addition of the magnitudes of the PSIF signal and of the FISP signal to form the respective overall magnitude $G_i$ for specific T2 values in msec. The curve 21 represents the result of the linear addition of the FISP signal and of the PSIF signal according to the traditional DESS method. The curve 23 shows the result of an addition according to Equation [Eq. 8]. W=3 and $\lambda$=2 were selected for the calculation. In the region I, the overall magnitude $G_i$ according to the method of the invention is comparable to the corresponding, traditional DESS value. The PSIF signal and the FISP signal are added essentially equally weighted. By contrast, for low T2 values in region II, the PSIF signal contribution is essentially suppressed, so that the overall magnitude $G_i$ is essentially identical to the FISP signal.

For r=0 and for the case of a magnitude subtraction, the following equation is obtained, this being particularly suited for weighting the known HIRE method:

$$G_i = X_i - W \cdot \left(\frac{Y_i}{X_{\max}}\right)^\lambda \cdot Y_i \qquad (\text{Eq. 9})$$

Figure 3:
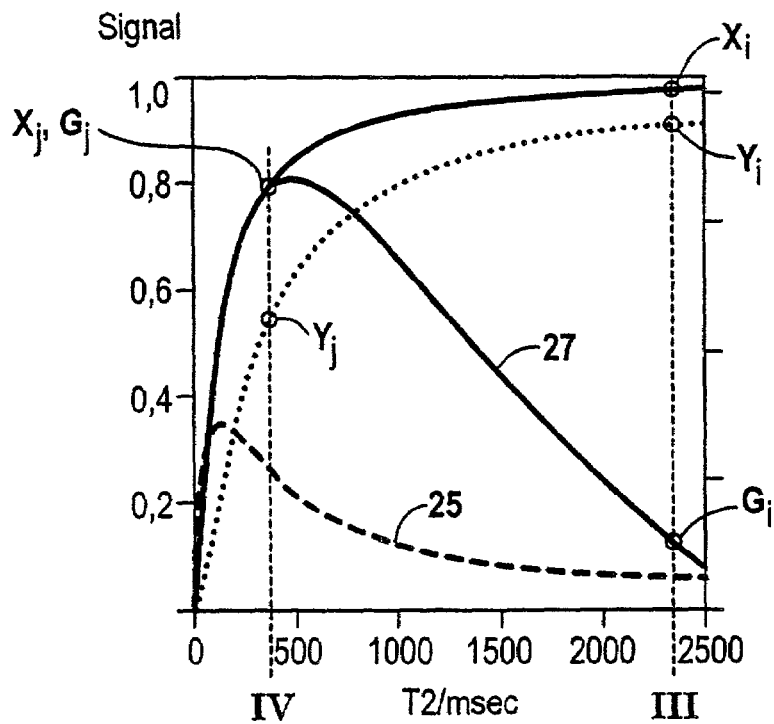
FIG. 3 illustrates a simulation of the method according to FIG. 1 employed in a HIRE method.

The T2-weighted, diagnostic signal is respectively employed as magnitude value $X_i$ of the picture elements i of the first image matrix BM1. The highly T2-weighted signal that, in particular, supplies a very high magnitude in CSF, is utilized as magnitude value $Y_i$ of a picture element i of the second matrix BM2. The result of such a calculation is shown in FIG. 3 as curve 27 for various T2 values (in msec), particularly for two different regions III, IV of the examination subject 7, respectively compared to a linear image subtraction ("HIRE (Standard)", curve 25). Curve 27 represents the overall magnitudes $G_i$ for various T2 values according to Equation [Eq. 9]. $\lambda=2$ and W=3 were again utilized. In region III, the same image subtraction essentially occurs in the method of the invention as in the traditional HIRE method. By contrast, no determining subtraction occurs in region IV.

Using the input unit 15 (see FIG. 1), the weighting factor W as well as the exponents e, f of the power of the appertaining magnitude values $X_i$, $Y_i$ or the exponent $\lambda$ substituting for the exponent e can be varied or set by an operator. The proportionality factor P can also be variable. There is thus the possibility of optimizing the self-weighting with empirical knowledge.

Figure 4:
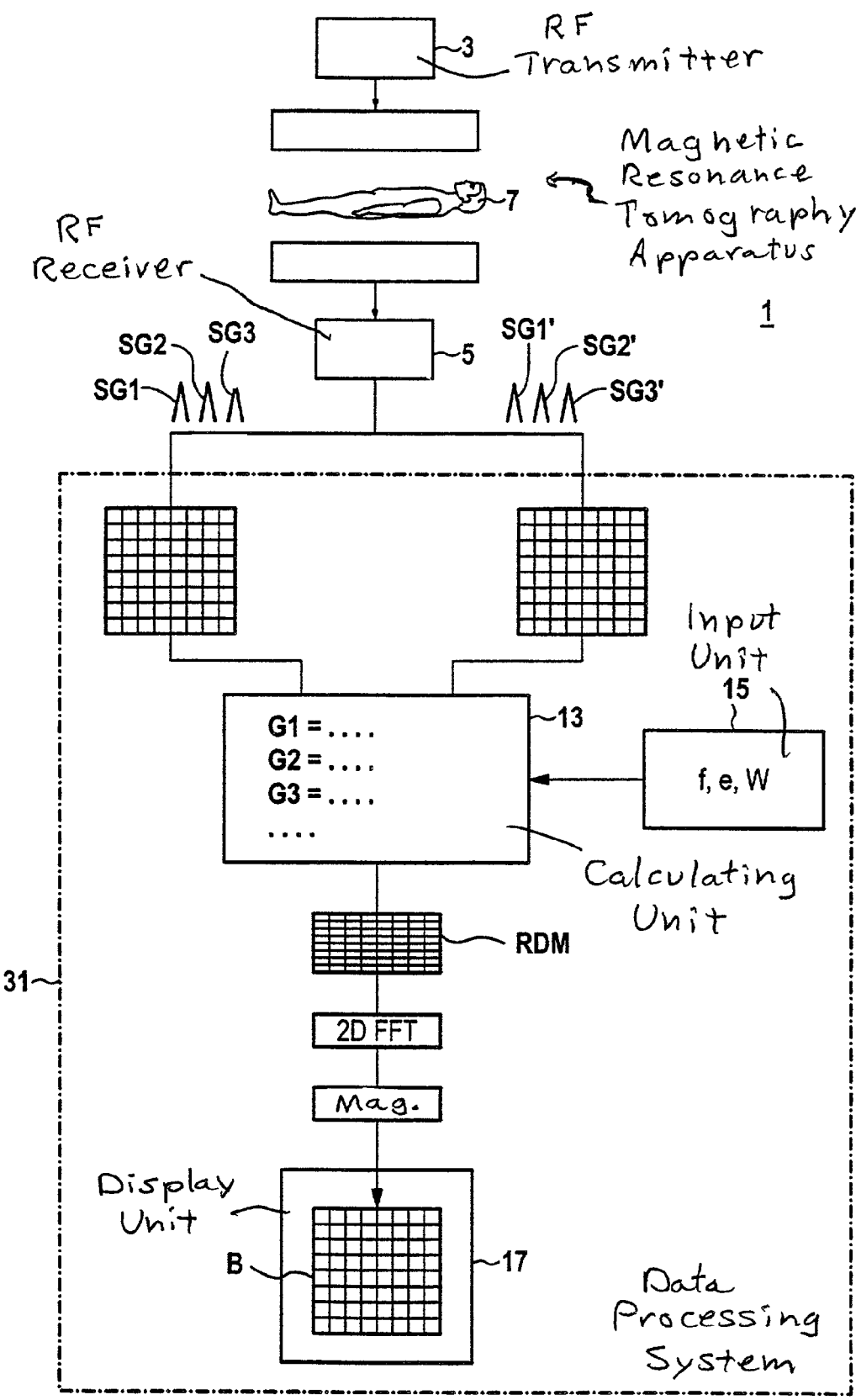
FIG. 4 is a flowchart of an exemplary second embodiment of the inventive method.

The explained, weighted addition or subtraction is capable of being implemented not only with magnitude values of image matrices BM1, BM2 but also with the original magnetic resonance signals SG1 through SG3 . . . or, respectively, SG1' through SG3' . . . This is schematically illustrated in FIG. 4. The magnetic resonance signals SG1 through SG3 of the first group and the magnetic resonance signals SG1' through SG3' of the second group are subtracted or added weighted in the calculating unit 13, whereby the exponents e, f and the weighting factor W can be set via the input unit 15. The result of the addition or subtraction, which is preferably undertaken corresponding to Equations 1 through 9, is the respective overall G1, G2, G3 . . . The result of the calculating procedure of the calculating unit 13 is a raw data matrix RDM that contains the overall signals G1, G2, G3 . . . as rows and that, following a Fourier transformation and magnitude formation, is converted into a matrix that generates the image B. This matrix is presented on the display unit 17.

The evaluation units 9, 11, the calculating unit 13 and/or the display unit 17 can be part of a data processing system 31 or of a computer.

Although modifications and changes may be suggested by those skilled in the art, it is in the intention of the inventor to embody within the patent warranted hereon all changes and modifications as reasonably and properly come within the scope of his contribution to the art.

I claim as my invention:

1. A method for generating an image from magnetic resonance signals comprising:

generating a first image matrix in k-space from first magnetic resonance signals, said first image matrix containing a plurality of picture elements each having a complex number magnitude value associated therewith, said first image matrix having an image quality;

generating a second image matrix in k-space from second magnetic resonance signals, different from said first magnetic resonance signals, said second image matrix containing a plurality of picture elements each having a complex number magnitude value associated therewith, said picture elements in said first image matrix respectively corresponding in matrix position to said picture elements in said second image matrix;

for each picture element in said first image matrix, forming a first real, non-weighted magnitude that is dependent on the complex number magnitude value for that picture element;

for each picture element in said second image matrix, forming a real, self-weighted second magnitude that is dependent on the complex number magnitude value of that picture element by multiplying said magnitude value for that picture element with a weighting factor, and setting said weighting factor, dependent on said magnitude value for that picture element of said second image matrix, to be higher if said magnitude value for that picture element is high than if said magnitude value for that picture element is low;

improving the image quality of the first image matrix by forming, for each of the respectively corresponding picture elements in said first image matrix and said second image matrix, an overall magnitude by mathematically combining said first magnitude and said second magnitude in a mathematical operation selected from the group consisting of addition and subtraction, thereby obtaining a plurality of overall magnitudes; and generating a final image from said overall magnitudes.

2. A method as claimed in claim 1 wherein the step of generating said first image matrix comprises reconstructing said first image matrix from a first group of location-coded magnetic resonance signals by Fourier transformation, and forming the respective magnitude values for the picture elements in said first image matrix after said Fourier transformation of said first group of location-coded magnetic resonance signals, and wherein the step of forming said second image matrix comprises reconstructing said second image matrix from a second group of location-coded magnetic resonance signals, different from said first group, by Fourier transformation, and forming the respective magnitude values of the picture elements in said second image matrix after said Fourier transformation of said second group of location-coded magnetic resonance signals.

3. A method as claimed in claim 1 wherein the step of forming said second magnitude for each picture element in said second image matrix comprises forming said second magnitude by applying a non-linear mathematical function to the magnitude value for the respective picture element.

4. A method as claimed in claim 3 wherein said non-linear mathematical function is an exponential power of the respective magnitude value for each picture element in said second image matrix, said exponential power having an exponent which is the same for all of said picture elements in said second image matrix, and which is greater than 1.

5. A method as claimed in claim 4 comprising employing an exponent in said exponential power which is greater than or equal to 2.

6. A method as claimed in claim 4 comprising selecting said exponent in said exponential power to produce a high contrast in said final image.

7. A method as claimed in claim 4 comprising selecting said exponent in said exponential power to make corrections in said first image matrix with said second image matrix.

8. A method as claimed in claim 1 comprising generating at least one further image matrix from magnetic resonance signals different from the magnetic resonance signals respectively used to generate said first image matrix and said second image matrix, said further image matrix having further picture elements each having a further magnitude value, and forming, for each further picture element, a further magnitude dependent on the further magnitude value for that further picture element in the same way as said first magnitudes are formed, and using said further magnitudes, together with said first magnitudes and said second magnitudes in said mathematical combination to form the respective overall magnitudes.

9. A method as claimed in claim 1 comprising generating at least one further image matrix from magnetic resonance signals different from the magnetic resonance signals respectively used to generate said first image matrix and said second image matrix, said further image matrix having further picture elements each having a further magnitude value, and forming, for each further picture element, a further magnitude dependent on the further magnitude value for that further picture element in the same way as said second magnitudes are formed, and using said further magnitudes, together with said first magnitudes and said second magnitudes in said mathematical combination to form the respective overall magnitudes.

10. A method as claimed in claim 1 comprising the additional step of producing said first magnetic resonance signals and said second magnetic resonance signals from respective pulse sequences sharing a common radio-frequency excitation pulse.

11. A method as claimed in claim 1 comprising generating said first image matrix from first magnetic resonance signals having a high signal density than said second magnetic resonance signals.

12. A method as claimed in claim 11 comprising generating said first image matrix from first magnetic resonance signals having a higher average signal density than said second magnetic resonance signals.

13. A method as claimed in claim 1 comprising forming the respective overall magnitudes by subtracting the respective second magnitudes from the respective first magnitudes, and using only magnetic resonance signals which would be subtracted from each other in a high-intensity reduction pulse sequence as the first and second magnetic resonance signals for respectively generating said first image matrix and said second image matrix.

14. A method as claimed in claim 13 comprising obtaining said first magnetic resonance signals and said second magnetic resonance signals from a subject containing both a first tissue having a first T2 time constant and a second tissue having a second T2 time constant with said second T2 time constant being significantly longer than said first T2 time constant, and acquiring said first and second magnetic resonance signals during a time span wherein cross-magnetization arising after an excitation of said first and second tissue decreases with said first and second time constants and acquiring said first magnetic resonance signals sooner after said excitation than said second magnetic resonance signals and acquiring said second magnetic resonance signals in a time interval in said time span wherein said second tissue supplies a more significant signal contribution than said first tissue.

15. A method as claimed in claim 1 comprising forming the respective overall magnitudes by addition of the respective first magnitudes and the respective second magnitudes, and employing only magnetic resonance signals which would be added in a double echo steady-state pulse sequence as said first and second magnetic resonance signals for respectively generating said first image matrix and said second image matrix.

16. A method as claimed in claim 15 comprising obtaining said first magnetic resonance signals using a gradient echo sequence and obtaining said second magnetic resonance signals from a quasi-spin echo sequence, in the same double echo steady-state pulse sequence.

17. A method as claimed in claim 16 comprising employing a fast imaging spin echo (FISP echo) sequence as said gradient echo sequence, and employing an inverse FISP pulse sequence as said quasi-spin echo sequence.

18. A method as claimed in claim 1 wherein the step of generating the respective overall magnitudes comprises generating each overall magnitude as $$X_i^f \pm P \cdot Y_i^e$$

wherein $X_i$ the magnitude value of a picture element i of said first image matrix, $Y_i$ is the corresponding magnitude value of a picture element i of said second image matrix, f and e are exponents and P is a proportionality factor, and wherein e is greater than 1.

19. A method as claimed in claim 18 wherein e is greater than f.

20. A method as claimed in claim 1 comprising employing a scaling factor for forming each second magnitude so that no picture element has a second magnitude which is greater than the magnitude value for that picture element.

21. A method as claimed in claim 20 comprising forming said scaling factor from a maximum value of the magnitude values of the respective picture elements of the first image matrix.

22. A method as claimed in claim 20 comprising obtaining a plurality of image matrices from magnetic resonance signals obtained from pulse sequences of a same type, each of said plurality of image matrices containing picture elements and each of said picture elements in said plurality of image matrices having a magnitude value, and forming said scaling factor from a maximum value of said magnitude values of said picture elements of said plurality of image matrices.

23. A method as claimed in claim 22 comprising deriving said plurality of image matrices from a common three-dimensional image.

24. A method as claimed in claim 1 comprising employing a further weighting factor for calculating the respective second magnitudes which is identical for all picture elements in said second image matrix and which has a value other than 1.

25. A method as claimed in claim 24 comprising employing a weighting factor which has a value greater than 1.

26. A method as claimed in claim 24 comprising selecting said weighting factor to produce a high contrast in said final image.

27. A method as claimed in claim 24 comprising selecting said weighting factor to correct said first image matrix with said second image matrix.

28. A method for generating an image from magnetic resonance signals comprising the steps of:
- obtaining a first group of location-coded magnetic resonance signals as complex numbers in k-space representing an image having an image quality associated therewith;
- obtaining a second group of location-coded magnetic resonance signals as complex numbers in k-space, different from said first group, said magnetic resonance signals in said second group having respective location codings corresponding to the respective location codings of the magnetic resonance signals in said first group;
- for each magnetic resonance signal in said first group, forming a first real, non-weighted magnitude from the respective complex numbers in k-space;
- for each magnetic resonance signal in said second group, forming a second self-weighted magnitude by multiplying that magnetic resonance signal in said second group with a weighting factor dependent on that magnetic resonance signal of said second group, with said weighting factor being higher if that magnetic resonance signal in said second group has a high value than if that magnetic resonance signal in said second group has a low value;
- improving the image quality associated with said first group by forming, for each of the magnetic resonance signals in said first group and said second group respectively having corresponding location coding, an overall signal by mathematically combining the first magnitude and the second magnitude in a mathematical operation, selected from the group consisting of addition and subtraction, thereby obtaining a plurality of overall signals; and
- generating a final image from said overall signals.

29. A method as claimed in claim 28 wherein the step of generating the respective second magnitudes comprises, for each magnetic resonance signal in said second group, forming a second magnitude by applying a non-linear function to that magnetic resonance signal in said second group.

30. A method as claimed in claim 28 comprising, for each of said magnetic resonance signals in said second group, forming said second magnitude as an exponential power of that magnetic resonance signal in said second group, said exponential power having an exponent which is the same for all of said magnetic resonance signals in said second group and which is greater than 1.

31. A method as claimed in claim 30 comprising employing an exponent which is greater than or equal to 2.

32. A method as claimed in claim 28 wherein the step of generating said final image from the respective overall signals comprises forming a raw data matrix from said overall signals, and Fourier transforming said raw data matrix to obtain a Fourier transform matrix, and generating said final image from said Fourier transform matrix.

33. An apparatus for generating an image from magnetic resonance signals comprising:
- a magnetic resonance scanner that obtains first magnetic resonance signals and second magnetic resonance signals, different from said first magnetic resonance signals, from a subject;
- a first image memory in which said first magnetic resonance signals are stored as complex numbers in k-space in a first image matrix, said first image matrix containing a plurality of picture elements each having a magnitude value associated therewith, said first image matrix having an image quality;
- a second image memory in which said second magnetic resonance signals are stored in a second image matrix, said second image matrix containing a plurality of picture elements each having a complex number magnitude value associated therewith, said picture elements in said first image matrix respectively corresponding in matrix position to said picture elements in said second image matrix;
- a data processor connected to said first and second image memories and having a calculating unit that, for each picture element in said first image matrix, forms a first real, non-weighted magnitude that is dependent on the complex number magnitude value for that picture element, and for each picture element in said second image matrix, forms a real, second magnitude that is dependent on the complex number magnitude value for that picture element by multiplying said magnitude value for that picture element with a weighting factor, and setting said weighting factor, dependent on said magnitude value for that picture element of said second image matrix, to be higher if said magnitude value for that picture element is high than if said magnitude value for that picture element is low, and said data processor improving the image quality of the first image matrix by forming, for each of the respectively corresponding picture elements in said first image matrix and said second image matrix, an overall magnitude by mathematically combining said first magnitude and said second magnitude in a mathematical operation selected from the group consisting of addition and subtraction, thereby obtaining a plurality of overall magnitudes, and generating a final image from said overall magnitudes; and
- a display connected to said data processor for displaying said final image.

34. An apparatus as claimed in claim 33 wherein said data processor generates said first image matrix by reconstructing said first image matrix from a first group of location-coded magnetic resonance signals by Fourier transformation, and wherein said calculating unit forms the respective magnitude values for the picture elements in said first image matrix after said Fourier transformation of said first group of location-coded magnetic resonance signals, and wherein said data processor forms said second image matrix by reconstructing said second image matrix from a second group of location-coded magnetic resonance signals, different from said first group, by Fourier transformation, and wherein said calculating unit forms the respective magnitude values of the picture elements in said second image matrix after said Fourier transformation of said second group of location-coded magnetic resonance signals.

35. An apparatus as claimed in claim 33 wherein said calculating unit forms said second magnitude for each picture element in said second image matrix by forming said second magnitude by applying a non-linear mathematical function to the magnitude value for the respective picture element, and wherein said calculating unit forms said overall magnitudes comprises forming said overall magnitudes also employing said non-linear mathematical function.

36. An apparatus as claimed in claim 35 wherein said calculating unit employs, as said non-linear mathematical function, an exponential power of the respective magnitude value for each picture element in said second image matrix, said exponential power having an exponent which is the same for all of said picture elements in said second image matrix, and which is greater than 1.

37. An apparatus as claimed in claim 36 wherein said calculating unit employs an exponent in said exponential power which is greater than or equal to 2.

38. An apparatus as claimed in claim 36 comprising an input unit allowing selection of said exponent in said exponential power to produce a high contrast in said final image.

39. An apparatus as claimed in claim 36 comprising an input unit allowing selection of said exponent in said exponential power to make corrections in said first image matrix with said second image matrix.

40. An apparatus as claimed in claim 36 wherein said exponent in said exponential power for forming the respective second magnitudes is a first exponent, and wherein said calculating unit forms said first magnitude for each of the picture elements in the first image matrix by, for each picture element in said first image matrix, forming said first magnitude as an exponential power, having a second exponent, of the respective magnitude value for that picture element, with said first exponent being larger than said second exponent.

41. An apparatus as claimed in claim 33 wherein said magnetic resonance scanner obtains further magnetic resonance signals different from the first magnetic resonance signals and said second magnetic resonance signals, and wherein said apparatus further comprises a further image memory wherein said further magnetic resonance signals are stored in a further image matrix having further picture elements each having a further magnitude value, said further image memory being connected to said data processor, and wherein said calculating unit forms, for each further picture element, a further magnitude dependent on the further magnitude value for that further picture element in the same way as said first magnitudes are formed, and uses said further magnitudes, together with said first magnitudes and said second magnitudes in said mathematical combination to form the respective overall magnitudes.

42. An apparatus as claimed in claim 33 wherein said magnetic resonance scanner obtains further magnetic resonance signals different from the first magnetic resonance signals and said second magnetic resonance signals, and wherein said apparatus further comprises a further image memory wherein said further magnetic resonance signals are stored in a further image matrix having further picture elements each having a further magnitude value, said further image memory being connected to said data processor, and wherein said calculating unit forms, for each further picture element, a further magnitude dependent on the further magnitude value for that further picture element in the same way as said second magnitudes are formed, and uses said further magnitudes, together with said first magnitudes and said second magnitudes in said mathematical combination to form the respective overall magnitudes.

43. An apparatus as claimed in claim 33 wherein said magnetic resonance scanner obtains said first magnetic resonance signals and said second magnetic resonance signals from respective pulse sequences sharing a common radio-frequency excitation pulse.

44. An apparatus as claimed in claim 33 wherein said magnetic resonance scanner obtains said first magnetic resonance signals with a higher signal intensity than said second magnetic resonance signals.

45. An apparatus as claimed in claim 44 wherein said magnetic resonance scanner obtains said first magnetic resonance signals with a higher signal intensity on average than said second magnetic resonance signals.

46. An apparatus as claimed in claim 33 wherein said calculating unit forms the respective overall magnitudes by subtracting the respective second magnitudes from the respective first magnitudes, and uses only magnetic resonance signals which would be subtracted from each other in a high-intensity reduction pulse sequence as the first and second magnetic resonance signals for respectively generating said first image matrix and said second image matrix.

47. An apparatus as claimed in claim 46 wherein said magnetic resonance scanner obtains said first magnetic resonance signals and said second magnetic resonance signals from a subject containing both a first tissue having a first T2 time constant and a second tissue having a second T2 time constant with said second T2 time constant being significantly longer than said first T2 time constant, and acquires said first and second magnetic resonance signals during a time span wherein cross-magnetization arising after an excitation of said first and second tissue decreases with said first and second time constants and acquiring said first magnetic resonance signals sooner after said excitation than said second magnetic resonance signals and acquires said second magnetic resonance signals in a time interval in said time span wherein said second tissue supplies a more significant signal contribution than said first tissue.

48. An apparatus as claimed in claim 33 wherein said calculating unit forms the respective overall magnitudes by addition of the respective first magnitudes and the respective second magnitudes, and employing only magnetic resonance signals which would be added in a double echo steady-state pulse sequence as said first and second magnetic resonance signals for respectively generating said first image matrix and said second image matrix.

49. An apparatus as claimed in claim 48 wherein said magnetic resonance scanner obtains said first magnetic resonance signals using a gradient echo sequence and obtains said second magnetic resonance signals from a quasi-spin echo sequence, in the same double echo steady-state pulse sequence.

50. An apparatus as claimed in claim 49 wherein said magnetic resonance scanner employs a fast imaging spin echo (FISP echo) sequence as said gradient echo sequence, and employs an inverse FISP pulse sequence as said quasi-spin echo sequence.

51. An apparatus as claimed in claim 33 wherein said calculating unit generates the respective overall magnitudes comprises generating each overall magnitude as $$X_i^f \pm P \cdot Y_i^e$$

wherein $X_i$ is the magnitude value of a picture element i of said first image matrix, $Y_i$ is the corresponding magnitude value of a picture element i of said second image matrix, f and e are exponents and P is a proportionality factor, and wherein e is greater than 1.

52. An apparatus as claimed in claim 51 wherein e is greater than f.

53. An apparatus as claimed in claim 33 wherein said calculating unit employs a scaling factor for forming each second magnitude so that no picture element has a second magnitude which is greater than the magnitude value for that picture element.

54. An apparatus as claimed in claim 53 wherein said calculating unit forms said scaling factor from a maximum value of the magnitude values of the respective picture elements of the first image matrix.

55. An apparatus as claimed in claim 33 wherein said magnetic resonance scanner obtains a plurality of sets of magnetic resonance signals using pulse sequences of a same type, and wherein said apparatus comprises a plurality of image memories in which said sets are stored respectively in a plurality of image matrices, each of said plurality of image matrices containing picture elements and each of said picture elements in said plurality of image matrices having a magnitude value, and wherein said calculating unit forms said scaling factor from a maximum value of said magnitude values of said picture elements of said plurality of image matrices.

56. An apparatus as claimed in claim 55 wherein said plurality of image matrices in combination represent a common three-dimensional image.

57. An apparatus as claimed in claim 33 wherein said calculating unit employs a weighting factor for calculating the respective second magnitudes which is identical for all picture elements in said second image matrix and which has a value other than 1.

58. An apparatus as claimed in claim 57 wherein said calculating unit employs a weighting factor which has a value greater than 1.

59. An apparatus as claimed in claim 57 comprising an input unit allowing selection of said weighting factor to produce a high contrast in said final image.

60. An apparatus as claimed in claim 57 comprising an input unit allowing selection of said weighting factor to correct said first image matrix with said second image matrix.

61. An apparatus for generating an image from magnetic resonance signals comprising:

a magnetic resonance scanner that obtains a first group of location-coded magnetic resonance signals as complex numbers in k-space and that obtains a second group of location-coded magnetic resonance signals as complex numbers in k-space, different from said first group, said magnetic resonance signals in said second group having respective location codings corresponding to the respective location codings of the magnetic resonance signals in said first group, and said first group having an imaging quality associated therewith;

a data processor connected to said magnetic resonance scanner having a calculating unit that forms, for each magnetic resonance signal in said first group, a first real, non-weighted magnitude from the respective complex numbers in k-space; and for each magnetic resonance signal in said second group, that forms a self-weighted second magnitude by multiplying that magnetic resonance signal in said second group with a weighting factor dependent on that magnetic resonance signal of said second group, with said weighting factor being higher if that magnetic resonance signal in said second group has a high value than if that magnetic resonance signal in said second group has a low value, and improving the image quality associated with said first group by forming, for each of the magnetic resonance signals in said first group and said second group respectively having corresponding location coding, an overall signal by mathematically combining the first magnitude and the second magnitude in a mathematical operation, selected from the group consisting of addition and subtraction, thereby obtaining a plurality of overall signals; and for generating a final image from said overall signals; and a display connected to said data processor for displaying said final image.

62. An apparatus as claimed in claim 61 wherein said calculating unit generates the respective second magnitudes comprises, for each magnetic resonance signal in said second group, by forming a second magnitude by applying a non-linear function to that magnetic resonance signal in said second group.

63. An apparatus as claimed in claim 61 wherein said calculating unit, for each of said magnetic resonance signals in said second group, forms said second magnitude as an exponential power of that magnetic resonance signal in said second group, said exponential power having an exponent which is the same for all of said magnetic resonance signals in said second group and which is greater than 1.

64. An apparatus as claimed in claim 63 wherein said calculating unit employs an exponent which is greater than or equal to 2.

65. An apparatus as claimed in claim 61 comprising a memory containing a raw data matrix formed from said overall signals, and a transformation unit for Fourier transforming said raw data matrix to obtain a Fourier transform matrix, and wherein said calculating unit generates said final image from said Fourier transform matrix.

66. A data processing system that generates an image from first magnetic resonance signals stored as complex numbers in k-space in a first image matrix, said first image matrix having an image quality and containing a plurality of picture elements each having a complex number magnitude value associated therewith, and from second magnetic resonance signals different from said first magnetic resonance signals, stored as complex numbers in k-space in a second image matrix, said second image matrix containing a plurality of picture elements each having a complex number magnitude value associated therewith, said picture elements in said first image matrix respectively corresponding in matrix position to said picture elements in said second image matrix, said data processing system being programmed to, for each picture element in said first image matrix, form a real, non-weighted first magnitude that is dependent on the complex number magnitude value for that picture element, and for each picture element in said second image matrix, to form a self-weighted real second magnitude that is dependent on the complex number magnitude value for that picture element by multiplying said magnitude value for that picture element with a weighting factor, and to set said weighting factor, dependent on said magnitude value for that picture element of said second image matrix, to be higher if said magnitude value for that picture element is high than if said magnitude value for that picture element is low, and to improve the image quality of the first image matrix by forming, for each of the respectively corresponding picture elements in said first image matrix and said second image matrix, an overall magnitude by mathematically combining said first magnitude and said second magnitude in a mathematical operation selected from the group consisting of addition and subtraction, thereby obtaining a plurality of overall magnitudes, and to generate a final image from said overall magnitudes.

67. A data processing system that generates an image from a first group of location-coded magnetic resonance signals represented as complex numbers in k-space, having an image quality associated therewith, and a second group of location-coded magnetic resonance signals represented as complex numbers in k-space different from said first group, said magnetic resonance signals in said second group having respective location codings corresponding to the respective location codings of the magnetic resonance signals in said first group, said data processor being programmed to, for each magnetic resonance signal in said first group, form a first real, non-weighted magnitude from the respective complex numbers and, for each magnetic resonance signal in said second group, to form a self-weighted real, second magnitude by multiplying that magnetic resonance signal in said second group with a weighting factor dependent on that magnetic resonance signal of said second group, with said weighting factor being higher if that magnetic resonance signal in said second group has a high value than if that magnetic resonance signal in said second group has a low value, and to improve the image quality associated with said first group by forming, for each of the magnetic resonance signals in said first group and said second group respectively having corresponding location coding, an overall signal by mathematically combining the first magnitude and the second magnitude in a mathematical operation, selected from the group consisting of addition and subtraction, thereby obtaining a plurality of overall signals, and to generate a final image from said overall signals.

* * * * *